United States Patent
Wang et al.

(10) Patent No.: US 7,245,369 B2
(45) Date of Patent: Jul. 17, 2007

(54) SPECTROSCOPIC APPARATUS USING SPECTRUM NARROWED AND STABILIZED LASER WITH BRAGG GRATING

(75) Inventors: Sean Xiaolu Wang, Wilmington, DE (US); Xin Jack Zhou, Hockessin, DE (US)

(73) Assignee: B & W Tek, Inc., Newark, DE (US)

( * ) Notice: Subject to any disclaimer, the term of this patent is extended or adjusted under 35 U.S.C. 154(b) by 223 days.

(21) Appl. No.: 10/985,981

(22) Filed: Nov. 12, 2004

(65) Prior Publication Data

US 2005/0105084 A1    May 19, 2005

Related U.S. Application Data

(60) Provisional application No. 60/519,268, filed on Nov. 13, 2003.

(51) Int. Cl.
    *G01J 3/44* (2006.01)
(52) U.S. Cl. .................. 356/301; 356/317; 356/318; 356/417
(58) Field of Classification Search ............. 356/301, 356/328, 317, 318, 334, 417, 73; 372/50.11, 372/50.12, 50.121, 102, 108
    See application file for complete search history.

(56) References Cited

U.S. PATENT DOCUMENTS

| 5,139,334 A | 8/1992 | Clarke |
|---|---|---|
| 5,651,018 A | 7/1997 | Mehuys et al. |
| 5,657,120 A | 8/1997 | Smith |
| 5,856,869 A | 1/1999 | Cooper et al. |
| 5,982,484 A | 11/1999 | Clarke et al. |
| 6,100,875 A | 8/2000 | Goodman et al. |
| 6,100,975 A | 8/2000 | Smith et al. |
| 6,563,854 B2 | 5/2003 | Tedesco |
| 6,610,351 B2 * | 8/2003 | Shchegolikhin et al. ........ 427/7 |
| 6,734,963 B2 * | 5/2004 | Gamble et al. ............. 356/301 |
| 2005/0018743 A1 | 1/2005 | Volodin et al. |

OTHER PUBLICATIONS

Angel, et al., The Utilization of Diode Lasers for Raman Spectroscopy:, 1995, Spectrochimica Acta Part A 51A 1995, pp. 1779-1799.
J. Funfschilling, et al., "CW Laser Wavelength Modulation in Raman and Site Selection Fluorescence Spectroscopy", Applied Spectroscopy, vol. 30, No. 4, 1976, pp. 443-446.
C. Allred, et al. "Near-Infrared Raman Spectroscopy of Liquids and Solids with a Fiber-Optic Sampler, Diode Laser, and CCD Detector", Spectroscopic Techniques, vol. 44, No. 7, 1990, Applied Spectroscopy, pp. 1129-1231.
A. Shreve, et al. "Effective Rejection and Fluorescence Interference in Raman Spectroscopy Using a Shifted Excitation Difference Technique", Spectroscopic Techniques, vol. 46, No. 4, 1992, Applied Spectroscpy, pp. 707-711.

* cited by examiner

*Primary Examiner*—Layla G. Lauchman
(74) *Attorney, Agent, or Firm*—Blank Rome LLP

(57) ABSTRACT

An apparatus for measuring properties of physical matters by means of Raman spectroscopy including a laser element, a wavelength dispersion element, an array or single element detector, and a control and data processing unit. The laser element, which is used to excite Raman scattering, is spectrum narrowed and stabilized by attachment of a Bragg grating device. The grating can be either a volume Bragg grating (VBG) written inside a glass substrate or a fiber Bragg grating (FBG) written inside an optical fiber. A laser element can be provided with a wavelength modulation capability for fluorescence background suppression.

48 Claims, 11 Drawing Sheets

VBG Enhanced Diode Laser

VBG Enhanced Diode Laser

FBG Enhanced Diode Laser

FBG Enhanced Diode Laser

VBG Enhanced DPSSL

VBG Enhanced DPSSL

SPECTROSCOPIC APPARATUS USING SPECTRUM NARROWED AND STABILIZED LASER WITH BRAGG GRATING

REFERENCE TO RELATED APPLICATION

The present application claims the benefit of U.S. Provisional Application No. 60/519,268, filed Nov. 13, 2003, whose disclosure is hereby incorporated by reference in its entirety into the present disclosure.

FIELD OF THE INVENTION

This invention generally relates to apparatus for analyzing substances by optical spectroscopy and, more specifically to Raman Spectroscopic apparatus using a spectrum narrowed and stabilized laser with Bragg gratings.

DESCRIPTION OF RELATED ART

Raman spectroscopy has become an effective analytical technique for chemical analysis. When a beam of monochromatic light is incident on a sample, some of the light is scattered by the material. Most of the scattered light does not exhibit a change in wavelength. This is called Rayleigh scattering. A tiny portion of the scattered light is shifted in wavelength by the molecular vibration and rotation of the molecules in the sample. This type of scattering is called Raman scattering, and the corresponding spectrum is called a Raman Spectrum. Raman spectra usually contain spectroscopic significant features that are characteristic of the molecules in the sample. Because of the unique Raman shift in the spectra, one can use it for qualitative analysis. What is more, the intensity of Raman spectra is directly related to the strength of molecular vibration and rotation. So the technique can also be used for quantitative analysis.

Since the generated Raman spectral intensity is linearly dependent on the excitation power, lasers have been the ideal excitation source of choice. In addition, the resolution of Raman spectrum is dependent on the spectral linewidth of the laser. An ideal laser would have narrow linewidth, stable spectral distribution and high power.

In the early years, due to the limitations of the available spectrometers and detectors, visible and ultra-violet wavelength gas lasers were used almost exclusively. However, the large physical size of these lasers, the difficulty in aligning optics, and the overall fragility of the systems limited Raman spectroscopy to be used as a laboratory analyzing method. Besides, the relatively short excitation laser wavelength often gave rise to intense and interfering fluorescence which obscured the weak Raman scattering.

In recent years, even with the arrival of the diode laser as the popular choice of Raman excitation source, the laser remains very expensive and delicate. As a result, Raman instruments are still not well suited for field uses, such as in industrial manufacturing or processing facilities.

The lack of a low cost, rugged, and stable diode laser remains a major barrier to develop a low cost and portable Raman instrument which can generate quality high resolution Raman spectrum. The main issues for diode lasers in Raman spectroscopic application are their spectral stability and spectral linewidth. A typical high power diode laser is a so-called Fabry-Perot (F-P) type laser in which the laser cavity is defined by the two cleaved facets of a diode chip. Due to the power density limitation, for an optical output power level larger than several hundreds of mW, a broad stripe (or broad area) structure is typically adopted with an emitter width of 50–200 μm. The inherent instability stems from a broad gain curve which allows multiple longitudinal modes and transverse modes to co-exist within the gain curve and with spatial distribution over the whole emitter width. The standard Fabry-Perot design does not allow for any discrimination between the modes, and consequently, many different lasing modes will be present at a given time. This alone dictates a low resolution spectrum when these lasers are used in Raman spectroscopy. Furthermore, these modes are constantly competing and inducing mode-hopping, which in turn affects the laser emission wavelength and spectral intensity distribution.

Clarke et al, (U.S. Pat. No. 5,139,334, "Hydrocarbon analysis based on low resolution Raman spectral analysis," Aug. 18, 1992 and U.S. Pat. No. 5,982,484, "Sample analysis using low resolution Raman spectroscopy," Nov. 9, 1999), introduced the concept of low resolution Raman spectroscopy (LRRS) by using a high power, broad area, F-P diode laser. However, due to the mode instability and relatively broad spectrum of a regular F-P diode laser, LRRS has only very limited utilities due to poor quality Raman spectrum generated.

The other two types of diode lasers, i.e., distributed feedback (DFB) and distributed Bragg reflector (DBR) lasers, incorporate wavelength discrimination mechanism for locking the laser to a single longitudinal mode or fewer longitudinal modes. These are monolithically integrated devices with embedded grating structure in gain region in case of the DFB diode laser and outside of gain region in case of the DBR diode laser. The application of DBR and DFB lasers in Raman spectroscopy has been disclosed by Cooper et al. in U.S. Pat. No. 5,856,869, "Distributed Bragg Reflector Diode Laser for Raman excitation and Method for Use," Jan. 5, 1999 and by A. Wang, L. A. Haskin and E. Cortez in "Prototype Raman spectroscopic sensor for in situ mineral characterization on planetary surfaces," Applied Spectroscopy, Vol. 52, No. 4, 477–487, 1998. However, these devices are typically difficult to manufacture and require high precision multi-epitaxial growth, therefore leading to high cost. Due also to the single spatial mode structure, the power level of these lasers is typically limited to be less than 200 mW in near infrared region. In addition, optical feedback can further introduce power instability and mode-hopping due to weak cavity and short cavity length (low cavity Q value).

Due to the limited power level of a DFB or DBR laser, some seeded-amplification techniques have been used to boost their power, such as a Master Oscillator Power Amplifier (MOPA) structure disclosed in "SDL-8530-785 nm, 300 mW CW Wavelength-Stabilized High Power Laser Diode System," SDL Product Catalog, pp. C5–C7 (1996/1997) and in U.S. Pat. No. 5,651,018, "Wavelength-stabilized, High Power Semiconductor Laser," Jul. 22, 1997 by Mehuys et al. However, due to complexity, high cost and low yield of the product, this product is not currently commercially available. Another scheme of injected seed locking was described in I. Shvarchuck, K. Dieckmann, M. Zielonkowski, and J. T. M. Walraven, "Broad-area diode laser system for a rubidium Bose-Einstein condensation experiment," Applied Physics B, B-71, 475–480, 2000. The system is quite complicated, and optical alignment is very delicate and difficult.

To achieve the desired spectral performance, an external cavity laser (ECL) can be built by placing a high power diode laser inside an external cavity. The typical configuration for this type of ECL is based on classical Littrow or Littman-Metcalf configuration ("Littrow vs. Littman laser, a comparison," Technical Note No.13, Sacher Lasertechnik).

The Littman configuration can achieve a narrower line width; however, the Littrow configuration which can achieve a higher output power is most popular for Raman spectroscopy. Examples of using Littrow ECL as the excitation source of Raman spectroscopy were described by Smith et al. in U.S. Pat. No. 5,657,120, "Laser diode system for Raman spectroscopy," Aug. 12, 1997 and U.S. Pat. No. 6,100,875, "Raman spectroscopy apparatus and method using external cavity laser for continuous chemical analysis of sample streams," Aug. 8, 2000, and more recently by Tedesco et al. in U.S. Pat. No. 6,563,854, "Integrated external diode laser module particularly suited to Raman spectroscopy", May 13, 2003. However, this type of ECL is quite delicate and vulnerable. Since the reflective grating which defines the length of cavity is relatively far from the laser chip, the cavity length is relatively long. Any slight change in the cavity mechanically or thermally can cause instability in emission wavelength.

SUMMARY OF THE INVENTION

It will be appreciated that a need exists in the art for a low cost Raman spectrometer for use outside of laboratory environment as a compact, rugged and portable instrument. It is therefore an object of the present invention to provide such a spectrometer and also to overcome the above-noted deficiencies of the prior art To achieve the above and other objects, the present invention provides an apparatus for measuring properties of physical matters (such as a sample) by means of Raman spectroscopy. The apparatus includes a laser element, a wavelength dispersion element, as well as an array or single element photo detector based spectrometer, plus a control and data processing unit such as a computer or microprocessor. The laser is used as an excitation source for generating Raman scattering off the sample being analyzed. The Raman spectrum is then collected and filtered to remove the Rayleigh scattering. The obtained spectrum that contains Raman signal is dispersed using the wavelength dispersion element such as a grating or prism that can be either stationary or scanning. The dispersed Raman spectrum is then detected using an array or single element photo detector based spectrometer. A microprocessor or computer processes the data from the spectrometer to analyze the composition and property of the sample.

The laser element disclosed in this invention is a novel spectrum narrowed and stabilized diode laser, or diode pumped solid-state laser, or fiber laser by attachment of a Bragg grating device which can be either a volume Bragg grating (VBG) written inside a glass substrate or a fiber Bragg grating (FBG) written inside an optical fiber. Unlike the previously demonstrated ECL, the VBG can be attached directly onto the diode laser chip, thus making the external cavity as short as possible, which in turn greatly improves the overall stability of the device.

Optical Bragg gratings are periodic refractive index modulations impressed in the volume of a glass or other light transmitting dielectric/semiconductor substrates. In order to create the grating structure, a photosensitive glass is usually used, whose refractive index can be modified either temporarily or permanently through optical radiation. Usually, the pattern of refractive index modulations inside the optical material is formed by interference effect generated by a UV laser. A VBG is induced by UV laser radiation to form a holographic pattern inside glass media. The glass media are then thermally treated to form refractive index modulation. The spectrum of a VBG is a Gaussian shape notch with about several percent to above 90% of reflectivity. The bandwidth can be as narrow as 0.2 nm or even narrower. The center wavelength of the notch can be tuned by rotating the VBG in reference to the incoming light. In another specific case, the grating is made in optical fibers and is called a FBG.

A uniform VBG reflects light only at a specific resonant wavelength, or so called Bragg wavelength. The Bragg wavelength is characteristic of the grating pitch and the field distribution of input light. In case of a FBG, the Bragg wavelength is also determined by the fiber parameters and guiding structures. A narrowband device has many applications, such as a notch reflector, band-stop filters, band-pass filters or spectrum slicing filter. All of these can be applied for achieving a narrowband diode or fiber laser.

As another aspect of the current invention, a multi-wavelength laser source with wavelength modulation capability can be built using the Bragg grating technology for fluorescence suppression in Raman spectroscopy.

DETAILED DESCRIPTION OF THE PREFERRED EMBODIMENTS

Preferred embodiments of the invention will now be set forth in detail with reference to the drawings.

Figure 1:
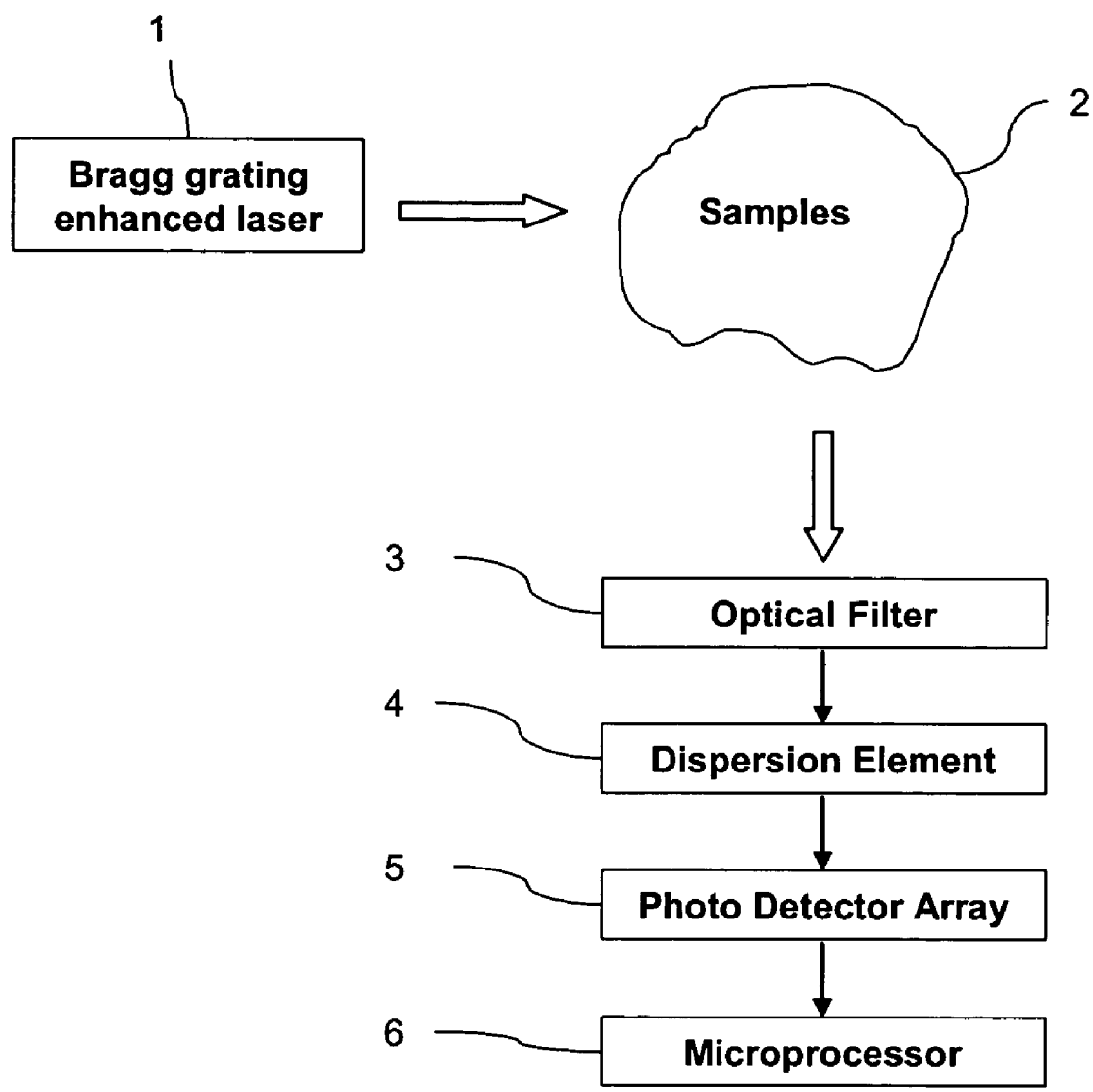
FIG. 1 is an example of a Raman spectrometer system using a Bragg grating enhanced diode laser as the excitation source.

An example of the disclosed Raman spectrometer is illustrated in FIG. 1. The apparatus includes a Bragg grating enhanced laser element 1, an optical filter element 3, a wavelength dispersion element 4, as well as an array or single element photo detector 5, plus a control and data processing unit such as a computer or microprocessor 6. This apparatus is used to measure the properties of the samples 2 by means of Raman spectroscopy. The laser 1 is used as an excitation source for generating Raman scattering off the sample 2 being analyzed. The Raman spectrum is then collected and filtered to remove the Rayleigh scattering. The obtained spectrum containing Raman signal is dispersed using the wavelength dispersion element 4 such as a grating or prism that can be either stationary or scanning. The dispersed Raman spectrum is then detected using an array photo detector or a single element photo detector 5 in case scanning dispersion element is used. A microprocessor or computer 6 processes the data from the spectrometer to analyze the composition and property of the sample 2.

Figure 2A:
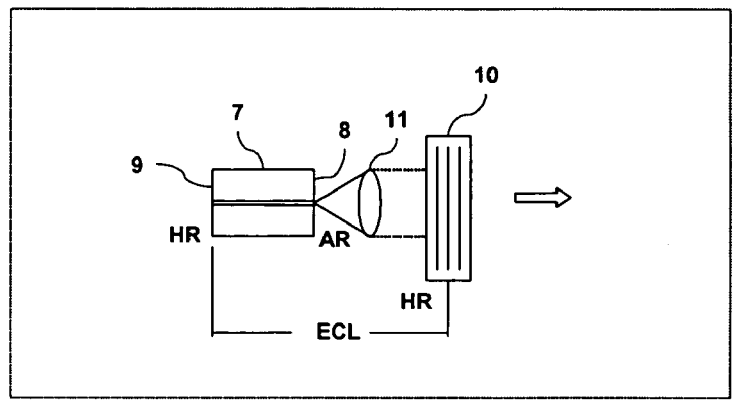
FIG. 2A illustrates a VBG enhanced diode laser configuration in the form of an external cavity laser (ECL).
Figure 2A:
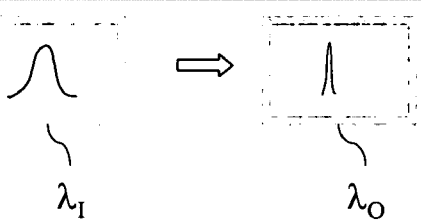
Figure 2B:
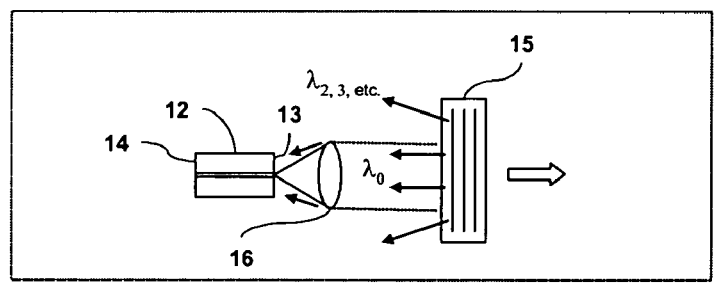
FIG. 2B illustrates a VBG enhanced diode laser configuration in the form of a self-seeded injection locking laser.
Figure 2B:
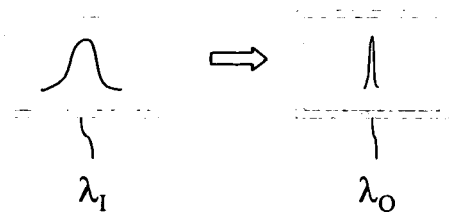

In one embodiment of the present invention, the laser element 1 is a F-P type diode laser. The laser can be a broad stripe diode laser to achieve high output power level. The spectral performance of the laser is enhanced by a VBG. The examples of two different variations of this embodiment are illustrated in FIG. 2A and FIG. 2B, respectively. In the figures, HR represents high-reflection and AR represents anti-reflection. FIG. 2A illustrates a VBG enhanced diode laser configuration in the form of an external cavity laser (ECL). In this configuration, the intrinsic cavity of the diode laser 7 is relatively weak due to relatively low reflectivity of the front facet 8 of the diode laser 7. The output beam of the diode laser 7 is first collimated by an optical element 11, such as a lens, and then transmitted to a VBG 10, which is a wavelength selective reflector. The VBG 10, together with the back facet 9 of the laser diodes, form an external cavity. In the figure, $\lambda_I$ is the original spectrum of the diode laser, and $\lambda_O$ is the spectrum after VBG enhancement. FIG. 2B illustrates a VBG enhanced diode laser configuration in the form of a self-seeded injection locking. In comparison to the ECL configuration, the reflectivity of the front facet 13 is relatively high (no special AR coating needed), and the selective wavelength reflection from VBG 15 may also be relatively low. The overall effect of VBG is to provide a seed injection (a narrow bandwidth spectral feedback) to the diode laser 12 so that it oscillates with a narrow, wavelength locked spectrum.

Figure 3A:
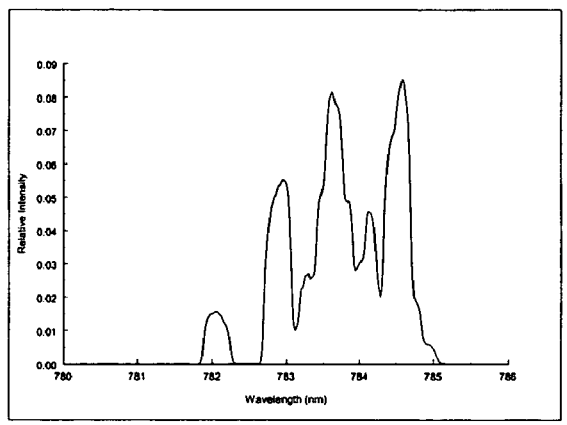
FIG. 3A is the spectrum of a regular F-P diode laser measured by an optical spectrum analyzer at a resolution of 0.05 nm.
Figure 3B:
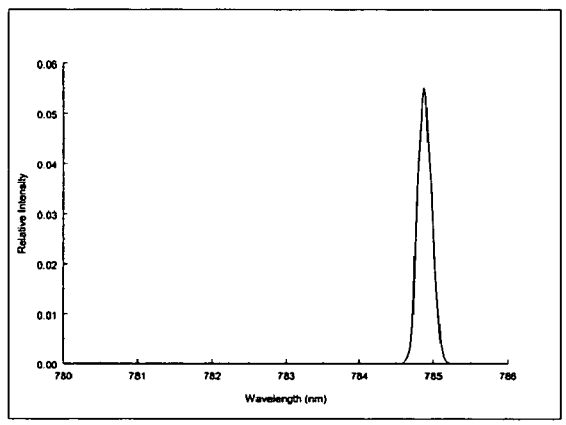
FIG. 3B is the spectrum of a VBG enhanced diode laser in ECL configuration measured by an optical spectrum analyzer at a resolution of 0.05 nm.
Figure 3C:
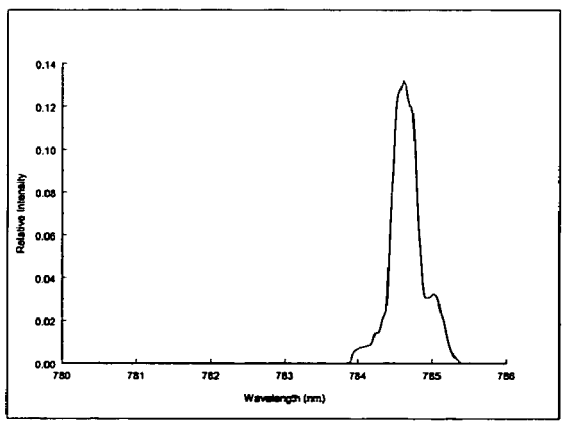
FIG. 3C is the spectrum of a VBG enhanced diode laser in injection locking configuration measured by an optical spectrum analyzer at a resolution of 0.05 nm.
Figure 4A:
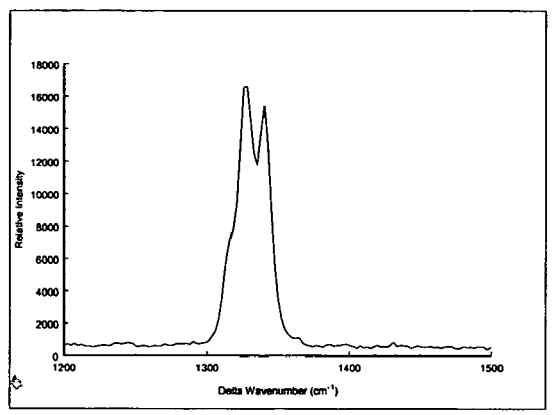
FIG. 4A is the Raman Spectrum of a diamond excited with a regular F-P diode laser. The resolution of the detection spectrometer is about 0.3 nm.
Figure 4B:
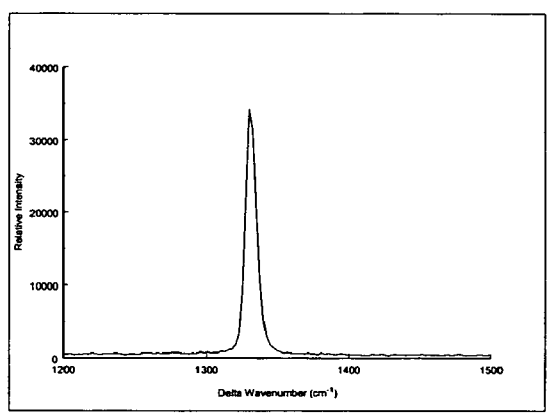
FIG. 4B is the Raman Spectrum of a diamond excited with a VBG enhanced diode laser in ECL configuration. The resolution of the detection spectrometer is about 0.3 nm.
Figure 4C:
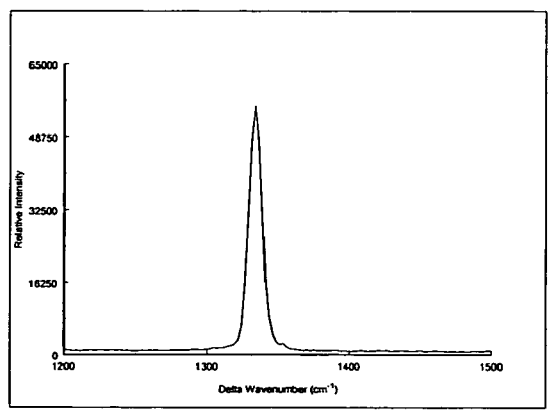
FIG. 4C is the Raman Spectrum of a diamond excited with a VBG enhance diode laser in injection locking configuration. The resolution of the detection spectrometer is about 0.3 nm
Figure 5A:
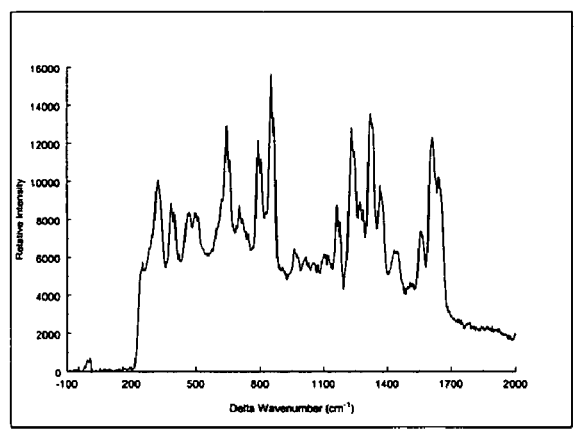
FIG. 5A is the Raman Spectrum of a Tylenol sample excited with a regular F-P diode laser. The resolution of the detection spectrometer is about 0.3 nm.
Figure 5B:
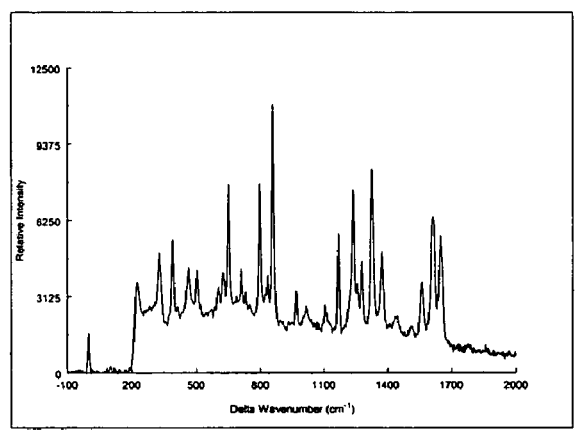
FIG. 5B is the Raman Spectrum of a Tylenol sample excited with a VBG enhanced diode laser in ECL configuration. The resolution of the detection spectrometer is about 0.3 nm.
Figure 5C:
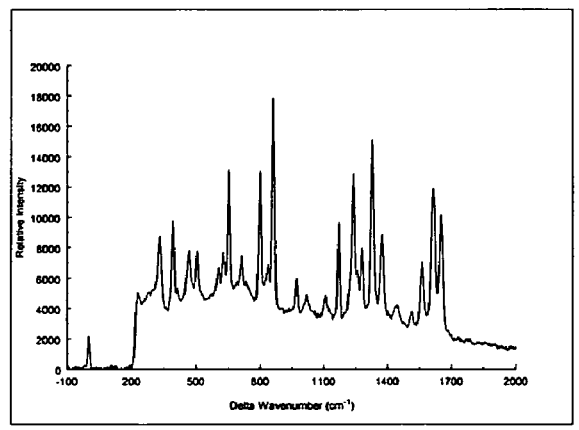
FIG. 5C is the Raman Spectrum of a Tylenol sample excited with a VBG enhance diode laser in injection locking configuration. The resolution of the detection spectrometer is about 0.3 nm.

The effect of VBG induced spectral enhancement is illustrated in FIGS. 3A–C. The spectra are measured by an optical spectrum analyzer at a resolution of 0.05 nm. FIG. 3A is the spectrum of a regular F-P diode laser. It is a gain-guided broad-stripe diode laser with an emitter size of 100 µm. The center wavelength of the diode laser is close to 785 nm. As shown clearly, there are multiple peaks inside a spectral profile of 2–3nm. FIG. 3B shows the spectrum of the VBG enhanced diode laser with a structure similar to FIG. 2A, in which an AR coating is used to reduce the front facet reflectivity down to be less than 0.1%. An ECL is formed by attaching a VBG close to the front facet of the diode laser. As clearly shown, the spectral linewidth is much narrower than that of FIG. 3A. Since the wavelength of the diode laser is locked by the VBG, its wavelength stability is also greatly improved. For example, the temperature sensitivity of the laser wavelength decreases from a typical value of 0.3 nm/° C. to as small as 0.01 nm/° C. FIG. 3C shows the spectrum of the VBG enhanced diode laser with a structure similar to FIG. 2B. The spectrum narrowing and stabilization are due to the so-called self-seeding mechanism. It is accomplished by means of relatively weak selective wavelength feedback into the diode laser gain region. Similarly to the ECL configuration, a VBG is placed close to the front facet (with a reflectivity about 3%) of the diode laser; however, special low reflection AR coating of the front facet is not necessary. The locking, narrowing and stabilization effect is weaker than that in case of ECL configuration.

The advantage of using VBG enhanced diode laser in a Raman spectrometer is further illustrated in FIGS. 4A–C and FIGS. 5A–C, in which the Raman spectra of a diamond and a Tylenol sample were obtained by use of regular and VBG enhanced diode laser excitation, respectively. The resolution of the detection spectrometer is about 0.3 nm. For the spectra obtained by regular F-P diode laser, there are artificial peaks created by side modes or impurity of the excitation laser spectrum. While the spectra obtained by VBG enhanced diode laser demonstrate much sharper and detailed Raman features reflecting much improved resolution over the ones without VBGs. The system diagram of the Raman spectrometer used in the experimentation is shown in FIG. 1.

In a slight variation of this embodiment, the VBG may be designed to reflect multiple wavelengths simultaneously. Thus a multiple wavelength Raman excitation source can be realized by integrating the VBG with a diode laser in a similar way as described in FIGS. 2A and 2B.

Figure 6A:
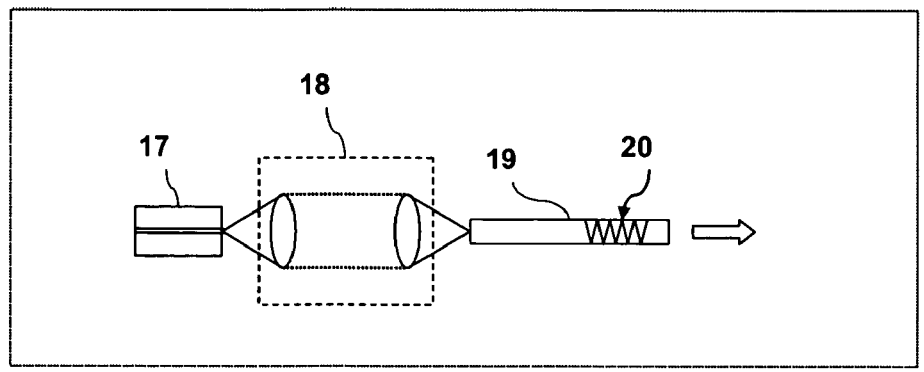
FIG. 6A illustrates a fiber Bragg grating (FBG) enhanced diode laser configuration.
Figure 6A:
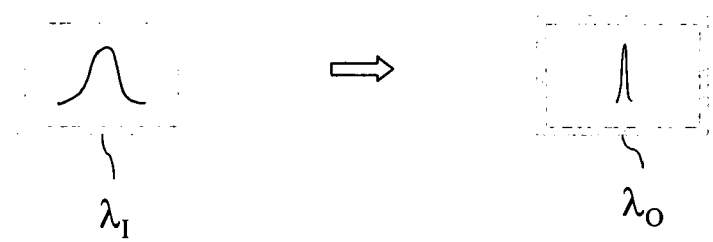
Figure 6B:
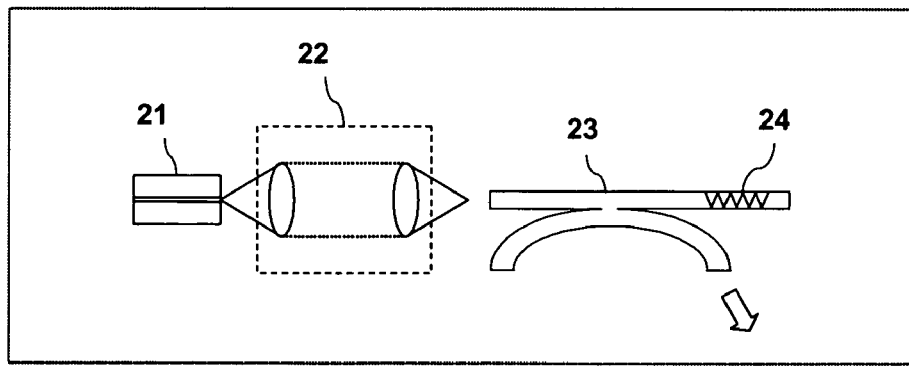
FIG. 6B illustrates another variation of a FBG enhanced diode laser.
Figure 6B:
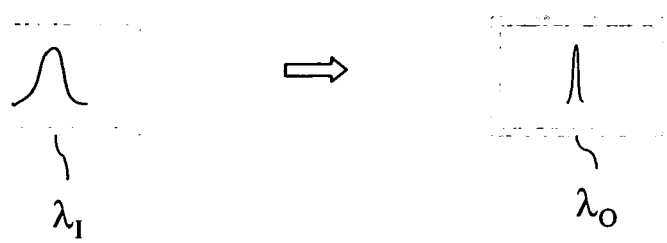

As another embodiment of the invention, a FBG enhanced diode laser can also be used in Raman spectroscopy. A schematic of this embodiment is illustrated in FIG. 6A. The output beam of the diode laser 17 is first collimated and transformed to match with the mode pattern of the optical fiber 19 by a group of lenses 18. The transformed beam is then coupled into the fiber 19. Part of the light is reflected back into the diode laser 17 by a FBG 20 written in the fiber at its resonant wavelength and serves as a feedback to lock the wavelength of the diode laser in a similar way as in FIGS. 2A–B. The locking of the wavelength can employ the mechanism of either self-seeding or ECL. In a slight variation of the embodiment as shown in FIG. 6B, the diode laser 21 is first collimated by the lenses 22 and transmitted into a fiber coupler 23. A FBG 24 is written in one arm of the fiber coupler and provide feedback to the diode laser 21. Another arm of the fiber coupler 23 is used for the output. In yet another embodiment of the invention, a fiber laser may replace the diode laser and be spectrally enhanced by one or multiple FBGs for Raman excitation use.

Figure 7:
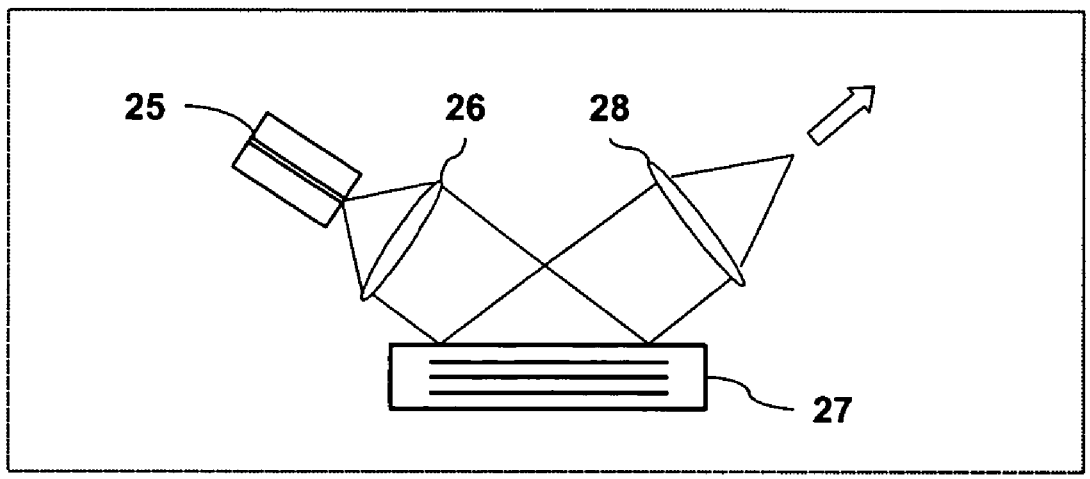
FIG. 7 illustrates a VBG enhanced super-luminescence-diode (SLD).
Figure 7:
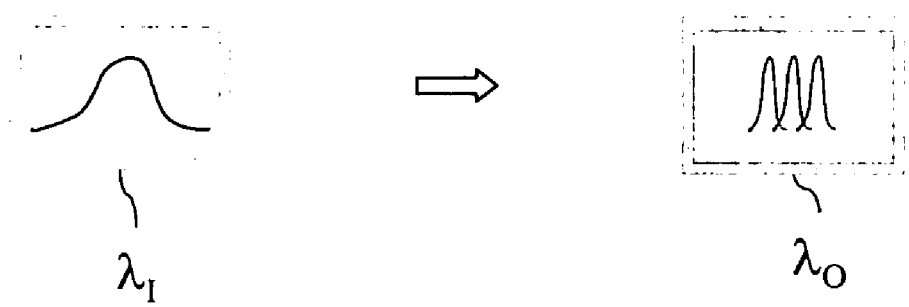

In yet another embodiment of the invention, a VBG enhanced super-luminescence-diode (SLD) may be used in which VBG functions as a spectrum slicing filter. A schematic view of the setup is shown in FIG. 7. The broadband output of the SLD 25 is first collimated by an optical element 26, such as a lens and shined on the VBG 27. The VBG 27 reflects part of the light within a narrow bandwidth around its resonant wavelength. The narrowband optical radiation is then collected by another lens 28 to excite Raman scattering on the sample. One or more narrowband optical radiation can thus be generated using VBG with single or multiple wavelength reflection so that single or multiple wavelength excitation sources can be realized. The similar effect may be also achieved by using this type of VBG with regular diode lasers.

Figure 8A:
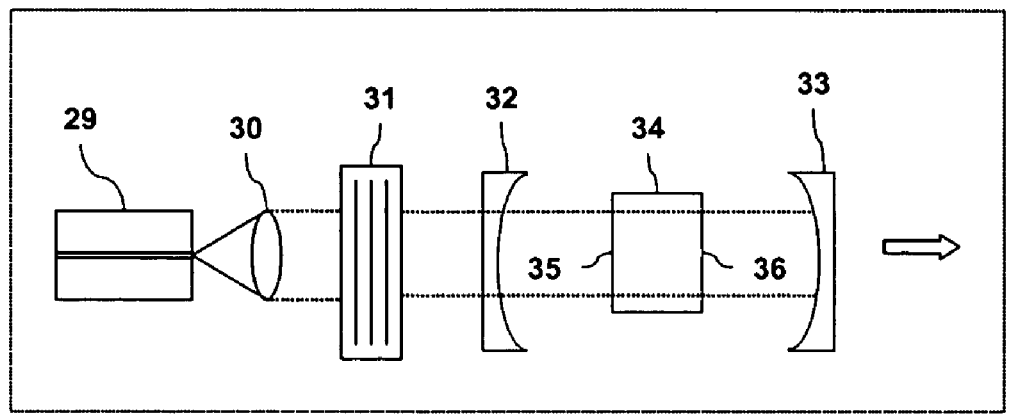
FIG. 8A illustrates a VBG enhanced diode-pumped solid-state laser (DPSSL).
Figure 8B:
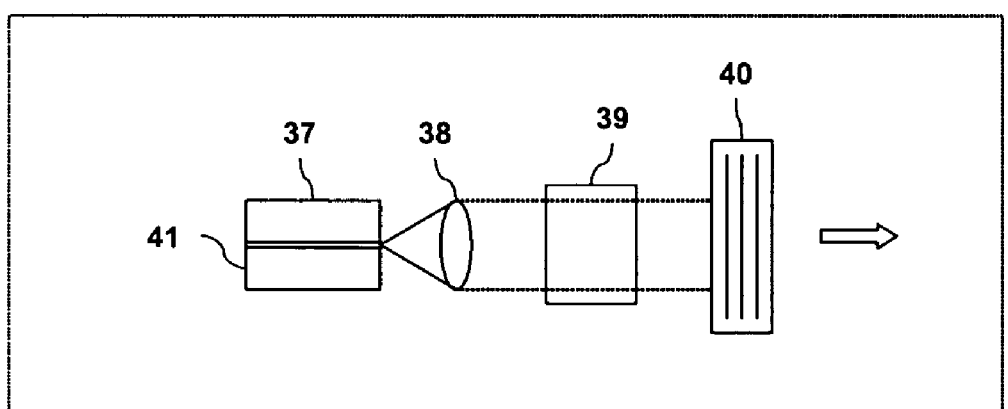
FIG. 8B illustrates another variation of the VBG enhanced DPSSL.

Yet another embodiment of the invention is a VBG enhanced solid-state laser, more specifically a diode-pumped solid-state laser (DPSSL). FIG. 8A illustrates one example of a VBG enhanced DPSSL. One or more spectrum narrowed and stabilized lasers comprising diode laser 29, collimating optical element 30 and VBG 31 are used for second harmonic generation (SHG) or frequency mixing in a nonlinear crystal 34. The laser cavity is formed by two mirrors 32, 33 or by the two facets 35, 36 of the crystal 34 when in absence of the two mirrors 32, 33. The crystal 34 can be a uniform bulk crystal or an optical non-linear medium with periodic structure for quasi-phase matching. The generated laser light with shorter wavelength, for example, in the green, blue, violet or ultra-violet (UV) wavelength region, can be employed for resonant Raman spectroscopy. Another variation of this embodiment is illustrated in FIG. 8B. In this configuration, the nonlinear crystal 39 is inserted between the collimating optical element 38 and the VBG 40. The laser cavity is formed by the VBG 40 and the back facet 41 of the diode laser 37.

In yet another embodiment, more than one VBG and/or FBG enhanced lasers may be combined to provide higher output power and/or sequential or simultaneous multiple wavelength excitation to achieve better signal to noise ratio (SNR), or to eliminate background noise such as fluorescence background, or to enable multi-dimensional spectroscopic analysis.

Figure 9:
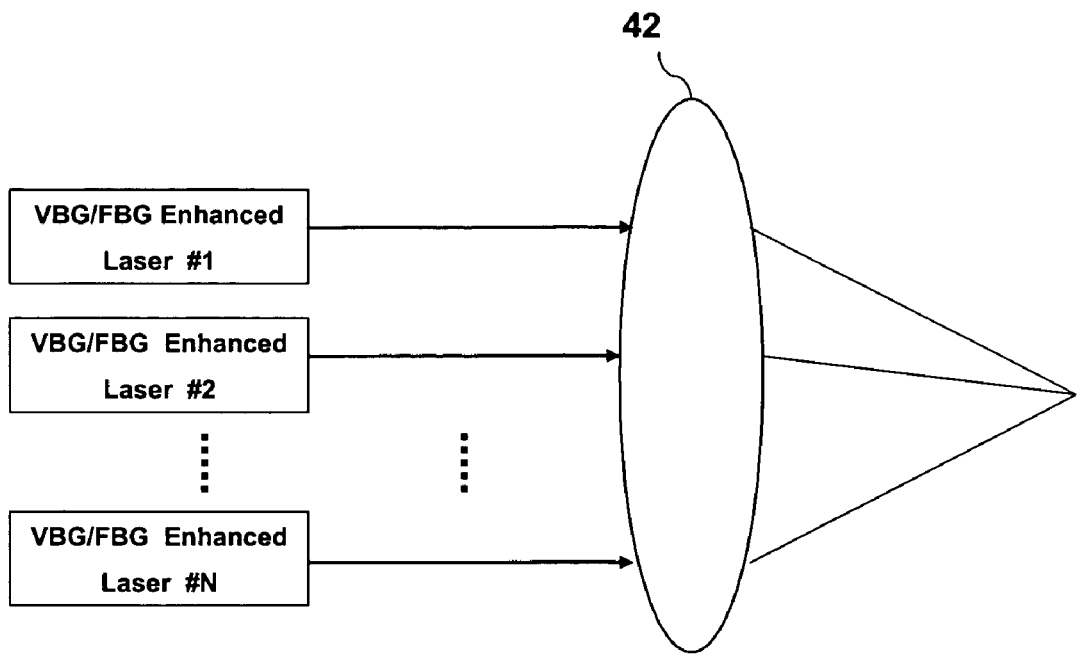
FIG. 9 illustrates a method for combining multiple VBG or FBG enhanced lasers in free space through a combining lens.

Combining multiple lasers may be done by means of free space multiplexing as illustrated in FIG. 9, in which the outputs of the lasers are combined by an optical element 42, such as a lens.

Figure 10:
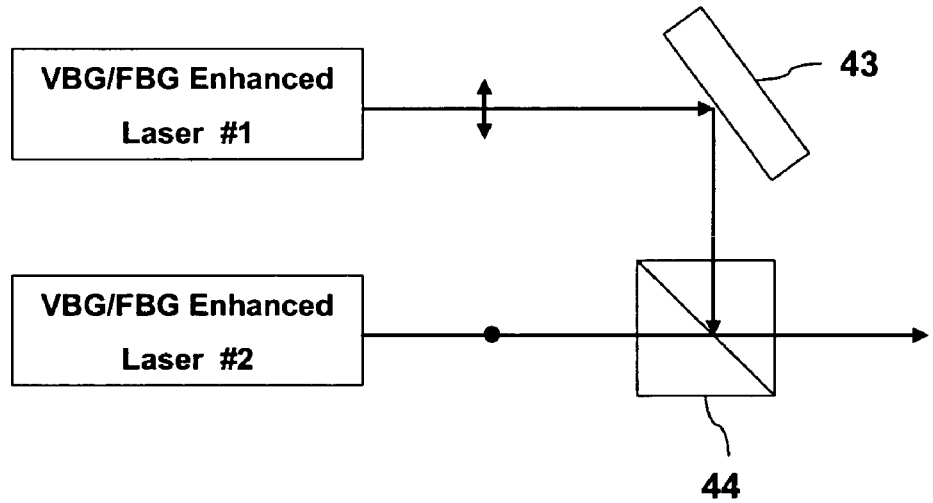
FIG. 10 illustrates a method for combining multiple VBG or FBG enhanced lasers through polarization combination.

Combing multiple lasers may be done by means of polarization multiplexing as illustrated in FIG. 10, in which the outputs of the lasers are combined by one or more mirrors 43 and a polarization beam splitter (PBS) 44.

Figure 11:
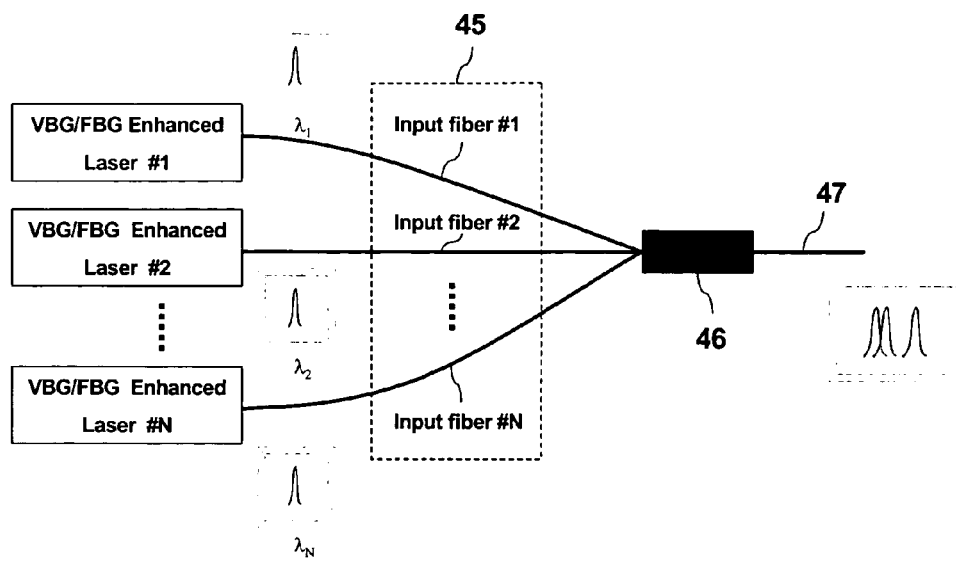
FIG. 11 illustrates a method for combing multiple VBG or FBG enhanced lasers using wavelength division multiplexing (WDM).

Combining multiple lasers may be done by means of wavelength domain multiplexing (WDM) as illustrated in FIG. 11, in which the outputs of the lasers are first coupled into an array of fibers 45 and then combined by a fiber optic coupler 46 into a single output fiber 47.

Figure 12:
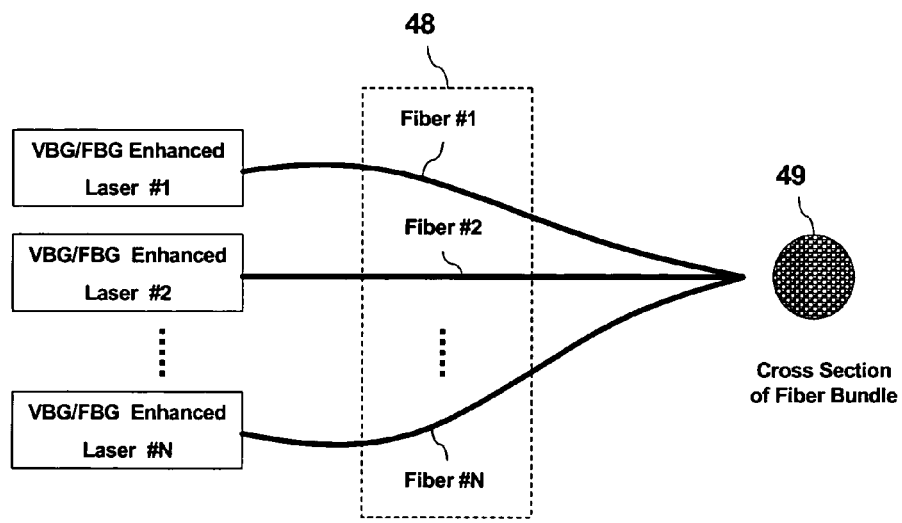
FIG. 12 illustrates a method for combining multiple VBG or FBG enhanced lasers using a fiber optical bundle.

Combining multiple lasers may also be done by means of multiple fiber bundling as illustrated in FIG. 12, in which the outputs of the lasers are first coupled into an array of fibers 48 and then combined directly into a fiber bundle 49.

Figure 13:
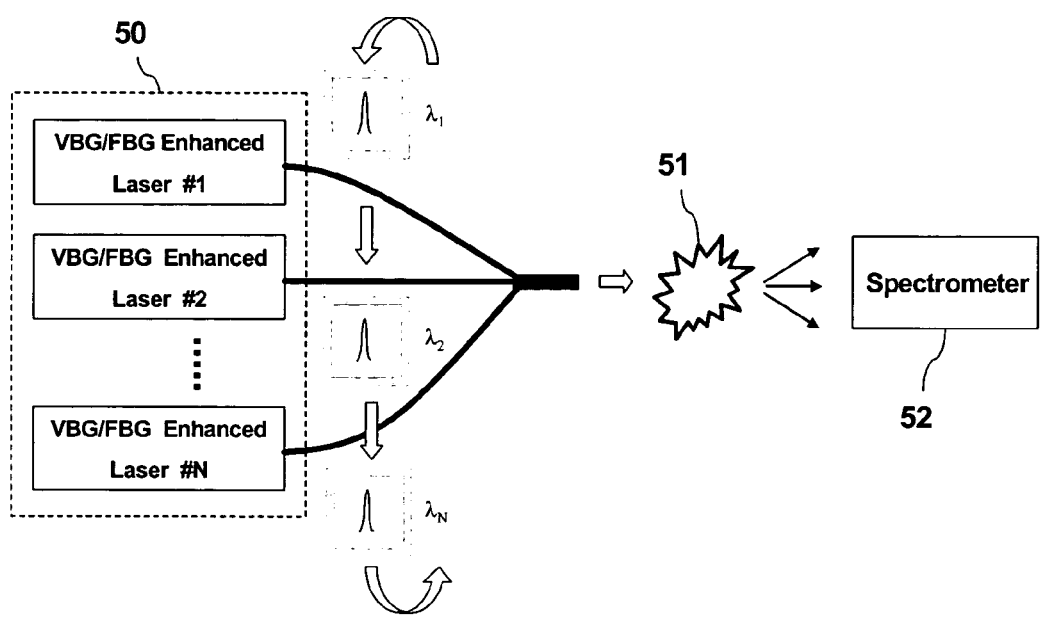
FIG. 13 illustrates a method for fluorescence suppression in Raman spectroscopy using wavelength modulation provided by a VBG/FBG enhanced laser array.

For a VBG/FBG enhanced diode laser, fiber laser or solid-state laser, the output wavelength is determined by the VBG/FBG, which can be easily tuned by varying the grating period. Thus by employing VBG/FBGs with different grating periods, a multiple wavelength laser array can be easily built even with similar diode lasers. One advantage of the multiple wavelength VBG/FBG enhanced laser array is its capability for fluorescence suppression in Raman spectroscopy. The technique can be implemented on a system such as the one illustrated in FIG. 13. The outputs of the multiple VBG/FBG enhanced lasers 50 are first combined using a method such as those mentioned above with reference to FIGS. 9–12. Each of the lasers keeps the same output power level and can be turned on/off independently by electronic control. The lasers are then shined on the sample 51 in a sequential manner at a certain excitation frequency, and the spectral variation of the scattered light is recorded by a spectrometer 52 similar to FIG. 1. Noting the fact that the shapes of the fluorescence spectra are generally independent of the precise excitation wavelength, while Raman peaks occur at a fixed wave number distance from the excitation band and mimics its wavelength distribution exactly, the spectral variation detected by the spectrometer is mainly caused by Raman scattering. Thus the fluorescence background can be easily filtered out by adopting frequency selective amplification/filtering of the detected signal at the excitation frequency, such as using a lock-in amplifier or through post processing by adopting digital filtering techniques. Either of those techniques, or any other, can be implemented in the spectrometer 52. The lasers used here can be in the form as shown in FIGS. 2A–B, FIG. 6 or FIGS. 8A–B. This technique is extremely suitable for short wavelength Raman spectroscopy such as in UV or visible region, where the fluorescence background often overwhelms the weak Raman signal.

In another embodiment, the invented apparatus can include a VBG or FBG enhanced laser, and the resulting Raman signal is detected using a Fourier Transform (FT) optical spectrometer for generating optical spectrum and measuring properties of samples.

In yet another embodiment, the invented apparatus can include a VBG or FBG enhanced laser, and the resulting Raman signal is detected using any optical spectrometer as far as it can measure the optical spectrum in the region of Raman signal, including but not limited to fixed filter, discrete filter set or tunable filter based optical spectrometers and other mathematical function transform based optical spectrometers. While various preferred embodiments have been set forth above, those skilled in the art who have reviewed the present disclosure will readily appreciate that other embodiments can be realized within the scope of the present invention. Therefore, the present invention should be construed as limited only by the appended claims.

We claim:

1. An apparatus for Raman spectroscopy of physical matter, the apparatus comprising:

(a) a spectrum narrowed and stabilized laser element for generating a laser beam and for causing the laser beam to enter the physical matter to stimulate Raman scattering in the physical matter and thereby to produce a Raman signal, the spectrum narrowed and stabilized laser element comprising a laser chip and a Bragg grating attached directly onto the laser chip;

(b) at least one optical filter, disposed in a path of the Raman signal, for removing Rayleigh scattering from the Raman signal to produce a filtered Raman signal;

(c) an optical spectrometer, disposed in a path of the filtered Raman signal, for measuring the spectrum of the Raman signal and for generating a detection signal; and (d) a microprocessor, connected to receive the detection signal, for determining properties of the physical matter from the detection signal.

2. The apparatus of claim 1, wherein the laser element comprises a diode laser.

3. The apparatus of claim 1, wherein the laser element comprises a solid-state laser.

4. The apparatus of claim 1, wherein the laser element comprises a fiber laser.

5. The apparatus of claim 1, wherein the Bragg grating is a volume Bragg grating.

6. The apparatus of claim 1, wherein the Bragg grating is a fiber Bragg grating.

7. The apparatus of claim 1, wherein the Bragg grating functions as a band-stop filter.

8. The apparatus of claim 1, wherein the Bragg grating functions as a band-pass filter.

9. The apparatus of claim 2, wherein the diode laser is spectrum narrowed and stabilized using said Bragg grating in external cavity configuration.

10. The apparatus of claim 9, wherein the Bragg grating is a volume Bragg grating.

11. The apparatus of claim 9, wherein the Bragg grating is a fiber Bragg grating.

12. The apparatus of claim 11, wherein the fiber Bragg grating exists in one arm of an optical fiber coupler, and wherein the other arm of said fiber coupler is used for laser output.

13. The apparatus of claim 2, wherein the diode laser is spectrum narrowed and stabilized using said Bragg grating in self-seeded injection locking configuration.

14. The apparatus of claim 3, wherein the solid-state laser is formed by disposing a nonlinear optical medium after a Bragg grating enhanced diode laser for frequency conversion.

15. The apparatus of claim 14, wherein the nonlinear optical medium is a uniform optical crystal.

16. The apparatus of claim 14, wherein the nonlinear optical medium has a periodic structure for quasi-phase matching.

17. The apparatus of claim 3, wherein the solid-state laser is formed by inserting a nonlinear optical medium between the diode laser and the Bragg grating for frequency conversion.

18. The apparatus of claim 1, wherein the Bragg grating possesses a single resonant wavelength.

19. The apparatus of claim 1, wherein the Bragg grating possesses a plurality of resonant wavelengths.

20. The apparatus of claim 1, wherein the optical spectrometer comprising:
   (a) a wavelength dispersion element, disposed in a path of the filtered Raman signal, for breaking down the filtered spectrum into wavelength or wave number components containing a Raman shifted signal with a dispersed Raman shift spectrum; and
   (b) a photo detector, disposed in a path of the Raman shifted signal, for detecting the dispersed Raman shift spectrum and for generating a detection signal.

21. The optical spectrometer of claim 20, wherein the dispersion element comprises a grating.

22. The optical spectrometer of claim 20, wherein the dispersion element compnses a prism.

23. The optical spectrometer of claim 20, wherein the detector comprises an array photo detector.

24. The optical spectrometer of claim 20, wherein the photo detector comprises a single element photo detector.

25. The apparatus of claim 1, wherein the optical spectrometer is a Fourier transform spectrometer.

26. The apparatus of claim 1, wherein the optical spectrometer is a fixed filter based spectrometer.

27. The apparatus of claim 1, wherein the optical spectrometer is a discrete filter set based spectrometer.

28. The apparatus of claim 1, wherein the optical spectrometer is a tunable filter based spectrometer.

29. The apparatus of claim 1, wherein the optical spectrometer is an optical transform based spectrometer.

30. The apparatus of claim 1, comprising a plurality of said laser elements.

31. The apparatus of claim 30, wherein the multiple laser elements have the same wavelength to achieve higher output power.

32. The apparatus of claim 30, wherein the multiple laser elements have different wavelengths.

33. The apparatus of claim 32, being used to achieve better signal to noise ratio.

34. The apparatus of claim 32, being used to eliminate background noise.

35. The apparatus of claim 32, being used for multi-dimensional spectroscopic analysis.

36. The apparatus of claim 30, further comprising a multiplexing element for multiplexing outputs of the lasers to form the laser beam.

37. The apparatus of claim 36, wherein the multiplexing element comprises a lens.

38. The apparatus of claim 36, wherein the multiplexing element comprises a polarizing combination.

39. The apparatus of claim 36, wherein the multiplexing element comprises a wavelength division multiplexer.

40. The apparatus of claim 36, wherein the multiplexing element comprises a fiber bundle.

41. An apparatus for Raman spectroscopy of physical matter, the apparatus comprising:
   (a) a Bragg grating enhanced super luminescence diode element for emitting light to be incident on the physical matter to stimulate Raman scattering in the physical matter and thereby to produce a Raman signal;
   (b) at least one optical filter, disposed in a path of the Raman signal, for removing Rayleigh scattering from the Raman signal to produce a filtered Raman signal;
   (c) an optical spectrometer, disposed in a path of the filtered Raman signal, for measuring the spectrum of the Raman signal and for generating a detection signal; and
   (d) a microprocessor, connected to receive the detection signal, for determining properties of the physical matter from the detection signal.

42. The apparatus of claim 41, wherein the Bragg gratings functions as a spectrum slicing filter.

43. A method for fluorescence suppression in Raman spectroscopy of a physical matter, comprising the steps of:
   (a) providing a multi-wavelength laser array by combining multiple Bragg grating enhanced lasers with different wavelengths to produce outputs, said different wavelengths being selected by using Bragg gratings having different grating periods;
   (b) shining the outputs of the lasers sequentially at certain frequency onto the physical matter to excite Raman scattering;
   (c) providing a Raman spectrometer to detect the excited Raman scattering and to generate a detection signal; and
   (d) amplifying/filtering the detection signal using a frequency selective amplification/filtering method tuned to said excitation frequency.

44. The method of claim 43, wherein the lasers are diode lasers.

45. The method of claim 43, wherein the lasers are solid-state lasers.

46. The method of claim 43, wherein the lasers are fiber lasers.

47. The method of claim 43, wherein step (d) is performed using a lock-in amplifier.

48. The method of claim 43, wherein step (d) is performed using a digital filtering technique.

* * * * *